US00PP33605P2

(12) United States Plant Patent
Trees

(10) Patent No.: US PP33,605 P2
(45) Date of Patent: Nov. 2, 2021

(54) ***LEUCANTHEMUM*PLANT NAMED 'WHITECAP'**

(50) Latin Name: ***Leucanthemum* x *superbum***
Varietal Denomination: Whitecap

(71) Applicant: SUNRISE FARM FLOWERS, LLC, Arroyo Grande, CA (US)

(72) Inventor: Scott C. Trees, Arroyo Grande, CA (US)

(73) Assignee: Sunrise Farm Flowers, LLC, Arroyo Grande, CA (US)

( * ) Notice: Subject to any disclaimer, the term of this patent is extended or adjusted under 35 U.S.C. 154(b) by 0 days.

(21) Appl. No.: 17/035,165

(22) Filed: Sep. 28, 2020

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
CPC ..... A01H 6/14
See application file for complete search history.

(56) References Cited

PUBLICATIONS

"Perennial Pulse, News and commentary on the global perennial plant market", downloaded from growertalks.com/Newsletters/view/newsletter/?article=3153, Apr. 21, 2020, pp. 1-13.*

* cited by examiner

*Primary Examiner* — Anne Marie Grunberg
(74) *Attorney, Agent, or Firm* — C. Anne Whealy

(57) ABSTRACT

A new and distinct cultivar of *Leucanthemum* plant named 'Whitecap', characterized by its relatively compact, upright and mounded plant habit; freely branching habit; strong and upright flowering stems; early, freely and continuous flowering habit; large single-type inflorescences with white-colored ray florets and large central yellow-colored disc; flower development that doesn't require vernalization; and good garden performance.

2 Drawing Sheets

Figure 1:
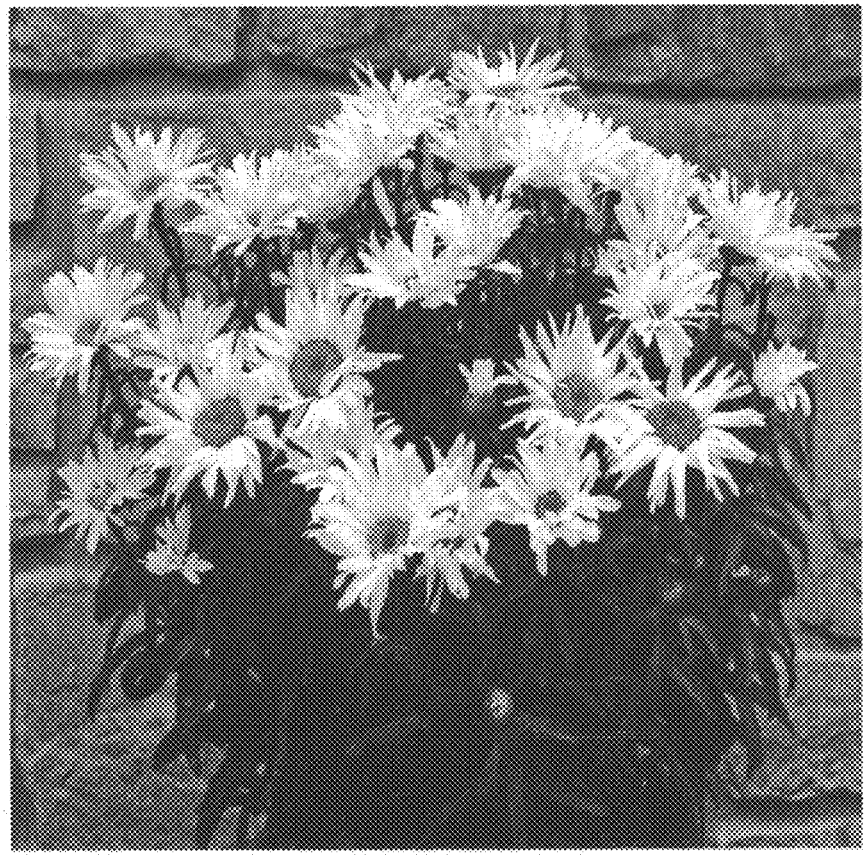

Botanical designation: *Leucanthemum* x *superbum*.
Cultivar denomination: 'WHITECAP'.

BACKGROUND OF THE INVENTION

The present invention relates to a new and distinct cultivar of *Leucanthemum* plant, botanically known as *Leucanthemum* x *superbum* and hereinafter referred to by the name 'Whitecap'.

The new *Leucanthemum* plant is a product of a planned breeding program conducted by the Inventor in Arroyo Grande, Calif. The objective of the breeding program is to create new *Leucanthemum* plants with a compact mounded habit, continuous flowering habit, numerous attractive single-type inflorescences and good garden performance.

The new Leucanthemum plant originated from an open-pollination in July, 2015 of *Leucanthemum* x *superbum* 'White Magic', disclosed in U.S. Plant Pat. No. 29,737, as the female, or seed, parent with an unknown selection of *Leucanthemum* x *superbum* as the male, or pollen, parent. The new *Leucanthemum* plant was discovered and selected by the Inventor as a single flowering plant from within the progeny of the stated open-pollination in a controlled environment in Arroyo Grande, Calif. in March, 2016.

Asexual reproduction of the new *Leucanthemum* plant by vegetative terminal cuttings in Arroyo Grande, Calif., since April, 2016 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Whitecap'. These characteristics in combination distinguish 'Whitecap' as a new and distinct *Leucanthemum* plant:

1. Relatively compact, upright and mounded plant habit.
2. Freely branching habit.
3. Strong and upright flowering stems.
4. Early, freely and continuous flowering habit.
5. Large single-type inflorescences with white-colored ray florets and large central yellow-colored disc.
6. No vernalization requirement for flowering.
7. Good garden performance.

Plants of the new *Leucanthemum* differ primarily from plants of the female parent, 'White Magic', in the following characteristics:

1. Plants of the new *Leucanthemum* are more compact and mounding than and not as tall and upright as plants of 'White Magic'.
2. Plants of the new *Leucanthemum* have single-type inflorescences whereas plants of 'White Magic' have semi-double inflorescences.

Plants of the new *Leucanthemum* can be compared to plants of *Leucanthemum* x *superbum* 'Snowcap', not patented. In side-by-side comparisons, plants of the new *Leucanthemum* differ from plants of 'Snowcap' in the following characteristics:

1. Plants of the new *Leucanthemum* are more vigorous than plants of 'Snowcap'.
2. Plants of the new *Leucanthemum* flower about two weeks earlier than plants of 'Snowcap'.
3. Plants of the new *Leucanthemum* flower more continously than plants of 'Snowcap'.
4. Plants of the new *Leucanthemum* have larger inflorescences than plants of 'Snowcap'.
5. Plants of the new *Leucanthemum* do not require vernaliztation for flowering whereas plants of 'Snowcap' require vernalization for flowering.
6. Plants of the new *Leucanthemum* do not produce any detectable fragrance whereas plants of 'Snowcap' produce the foul fragrance typical of *Leucanthemum* plants.

Plants of the new *Leucanthemum* can also be compared to plants of *Leucanthemum* x *superbum* 'Becky', not patented. In side-by-side comparisons, plants of the new *Leucanthemum* differ from plants of 'Becky' in the following characteristics:

1. Plants of the new *Leucanthemum* are more vigorous than plants of 'Becky'.
2. Plants of the new *Leucanthemum* flower about two weeks earlier than plants of 'Becky'.
3. Plants of the new *Leucanthemum* have larger inflorescences than plants of 'Becky'.
4. Plants of the new *Leucanthemum* do not require vernaliztation for flowering whereas plants of 'Becky' require vernalization for flowering.
5. Plants of the new *Leucanthemum* do not produce any detectable fragrance whereas plants of 'Becky' produce the foul fragrance typical of *Leucanthemum* plants.

BRIEF DESCRIPTION OF THE PHOTOGRAPHS

The accompanying colored photographs illustrate the overall appearance of the new *Leucanthemum* plant showing the colors as true as it is reasonably possible to obtain in colored reproductions of this type. Colors in the photographs may differ slightly from the color values cited in the detailed botanical description which accurately describe the colors of the new *Leucanthemum* plant.

The photograph on the first sheet (FIG. 1) is a side perspective view of a typical flowering plant of 'Whitecap' grown in a container.

Figure 2:
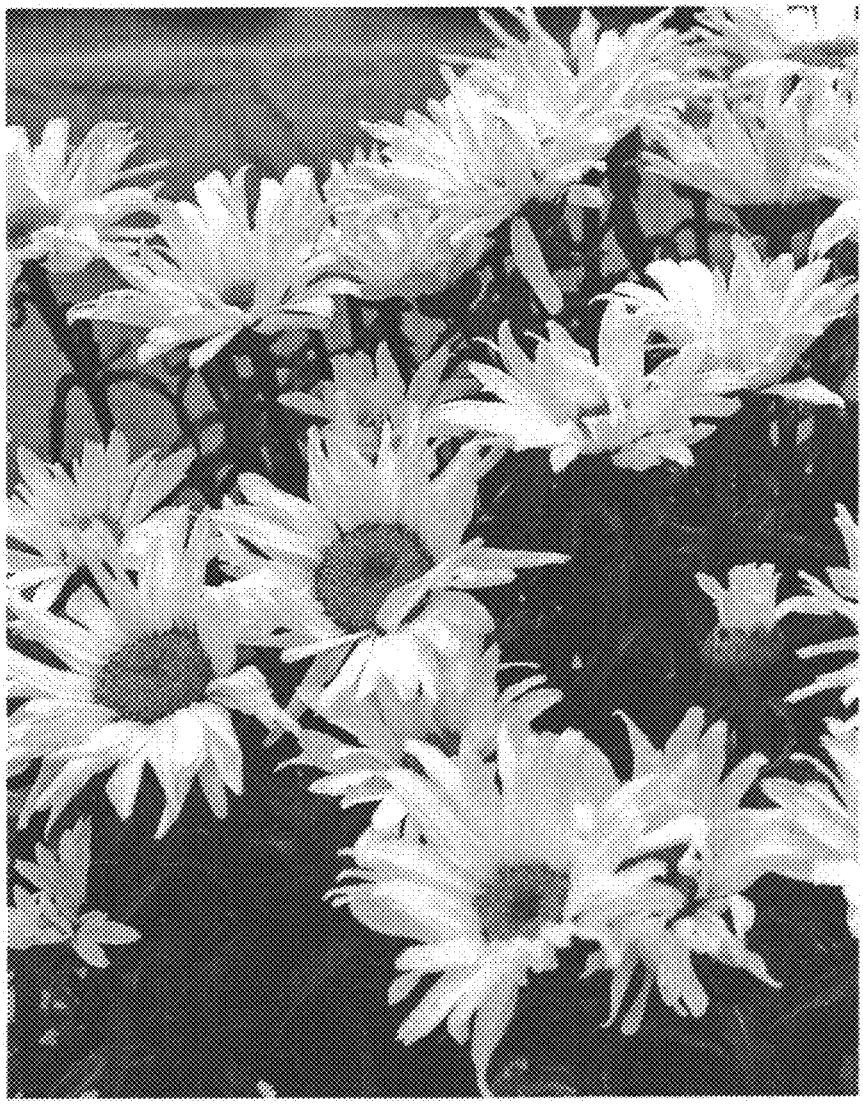

The photograph on the second sheet (FIG. 2) is a close-up view of a typical flowering plant of 'Whitecap'.

DETAILED BOTANICAL DESCRIPTION

The aforementioned photographs and following observations and measurements describe plants grown in one-gallon containers during the spring in a glass-covered greenhouse in Elburn, Ill. and under cultural practices typical of commercial *Leucanthemum* production. During the production of the plants, day temperatures averaged 16° C., night temperatures averaged 13° C. and light levels averaged 2,500 foot-candles. Plants were 19 weeks old when the photographs were taken and 20 weeks old when the description was taken. In the following description, color references are made to The Royal Horticultural Society Colour Chart, 2015 Edition, except where general terms of ordinary dictionary significance are used.

Botanical classification: *Leucanthemum* x *superbum* 'Whitecap'.

Parentage:

*Female, or seed, parent.*—*Leucanthemum* x *superbum* 'White Magic', disclosed in U.S. Plant Pat. No. 29,737.

*Male, or pollen, parent.*—Unknown selection of *Leucanthemum* x *superbum,* not patented.

Propagation:

*Type.*—Terminal vegetative cuttings.

*Time to initiate roots, summer.*—About five days at soil temperatures about 27° C.

*Time to initiate roots, winter.*—About ten days at soil temperatures about 21° C.

*Time to produce a rooted young plant, summer.*—About three weeks at soil temperatures about 27° C.

*Time to produce a rooted young plant, winter.*—About five weeks at soil temperatures about 22° C.

*Root description.*—Medium in thickness, semi-fleshy; typically creamy white to light brown in color, actual color of the roots is dependent on substrate composition, water quality, fertilizer type and formulation, substrate temperature and physiological age of roots.

*Rooting habit.*—Freely branching, dense; rapid root system development.

Plant description:

*Plant and growth habit.*—Herbaceous perennial; relativly compact, upright and mounded plant habit; vigorous growth habit; moderate growth rate; freely branching habit with about 10 to 15 primary branches each with numerous secondary branches developing per plant.

*Plant height.*—About 32.5 cm.

*Plant width.*—About 31 cm.

*Branch description.*—Length: About 30 cm. Diameter, at the base: About 6.5 mm. Internode length: About 1.5 cm to 2.5 cm. Strength: Strong. Aspect: Erect to about 30° from vertical. Texture and luster: Sparsely pubescent; semi-glossy. Color: Close to 137C.

*Leaf description.*—Arrangement: Alternate; simple; sessile. Length: About 9.5 cm. Width: About 1.5 cm to 2.5 cm. Shape: Oblanceolate to oblong. Apex: Acute. Base: Attenuate. Margin: Serrate. Texture and luster, upper surface: Smooth, glabrous; slightly glossy. Texture and luster, lower surface: Sparsely pubescent; matte. Venation pattern: Prominent midvein; reticulate. Color: Developing leaves, upper surface: Close to 146A. Developing leaves, lower surface: Close to 146B. Fully developed leaves, upper surface: Close to 147A; venation, close to 147B. Fully developed leaves, lower surface: Close to 146A to 146B; venation, close to 146A to 146B.

Inflorescence description:

*Appearance.*—Large single-type inflorescences with lanceolate-shaped ray florets and tubular disc florets; inflorescences held upright on strong peduncles, inflorescences face mostly upright; ray and disc florets develop acropetally on a capitulum.

*Fragrance.*—None detected.

*Flowering response.*—Plants begin flowering about twelve weeks after planting; plants flower continuously from the spring into the summer in California.

*Postproduction longevity.*—Inflorescences maintain good substance for several weeks on the plant; inflorescences persistent.

*Quantity of inflorescences.*—Freely flowering habit, about 48 inflorescences develop per plant during the flowering season.

*Inflorescence size.*—Diameter: About 6.5 cm. Depth (height): About 3 cm. Disc diameter: About 2 cm.

*Receptacles.*—Height: About 5 mm. Diameter: About 1.25 cm. Color: Close to 144B to 144C.

*Inflorescence buds.*—Height: About 5 mm. Diameter: About 1 cm. Shape: Flattened sphere. Color: Close to 144A.

*Ray florets.*—Quantity per inflorescence: About 36 arranged in a single whorl. Length: About 3.2 cm. Width: About 7 mm. Shape: Lanceolate. Apex: Acute or emarginate. Base: Attenuate. Margin: Entire; distally, slightly undulate. Aspect: Somewhat twisting; reflexing. Texture and luster, upper and lower surfaces: Smooth, glabrous; matte. Color: When opening and fully opened, upper surface: Close to NN155D; color does not change with development. When opening and fully opened, lower surface: Close to NN155D; color does not change with development.

*Disc florets.*—Quantity per inflorescence: About 320 massed at the center of the receptacle arranged in numerous whorls. Length: About 8 mm. Diameter: About 1 mm. Shape: Fused tubular. Apex: Acute, five-pointed. Texture and luster, inner and outer surfaces: Smooth, glabrous; slightly glossy. Color: When opening and fully opened, inner surface: Close to 12A; color does not change with development. When opening and fully opened, outer surface: Close to 14A; color does not change with development.

*Involucral bracts.*—Quantity per inflorescence: About 42 arranged in about three whorls. Length: About 7.5 mm. Width: About 3 mm. Shape: Oblong. Apex: Lanceolate. Base: Fused. Margin: Entire, membraneous. Texture and luster, upper and lower surfaces: Smooth, glabrous; somewhat glossy. Color, upper surface: Close to 144A. Color, lower surface: Close to 144B.

*Peduncles.*—Length: About 30 cm. Diameter, at the base: About 6.5 mm. Strength: Strong. Aspect: Upright to about 30° from vertical. Texture and luster: Sparsely pubescent; semi-glossy. Color: Close to 137C.

*Reproductive organs.*—Androecium: Present on disc florets only. Quantity per floret: Five per disc floret. Filament length: About 4.5 mm. Filament color: Close to 145C. Anther shape: Roughly rectangular. Anther length: About 1.5 mm. Anther color: Close to 10A. Pollen amount: Sparse. Pollen color: Close to 17A. Gynoecium: Present on ray, trans and disc florets. Quantity per floret: One. Pistil length: About 5 mm. Stigma diameter: Close to 1 mm. Stigma shape: Bi-parted. Stigma color: Close to 12A to 12B. Style length: About 4 mm. Style color: Close to 154C to 154D. Ovary color: Close to 145C.

*Seeds and fruits.*—To date, seed and fruit development have not been observed on plants of the new *Leucanthemum.*

Pathogen & pest resistance: To date, plants of the new *Leucanthemum* have not been observed to be resistant to pathogens and pests common to *Leucanthemum* plants.

Garden performance: Plants of the new *Leucanthemum* have been observed to have good garden performance and to tolerate wind and rain, to tolerate temperatures ranging from −15° C. to 35° C.

It is claimed:

1. A new and distinct *Leucanthemum* plant named 'Whitecap' as illustrated and described.

* * * * *